United States Patent
Anson

(10) Patent No.: US 6,706,064 B1
(45) Date of Patent: Mar. 16, 2004

(54) EXPANDABLE DEVICE

(75) Inventor: Anthony Walter Anson, Hounslow (GB)

(73) Assignee: Anson Medical Limited (GB)

( * ) Notice: Subject to any disclaimer, the term of this patent is extended or adjusted under 35 U.S.C. 154(b) by 0 days.

(21) Appl. No.: 09/446,833

(22) PCT Filed: Jun. 24, 1998

(86) PCT No.: PCT/GB98/01850
§ 371 (c)(1),
(2), (4) Date: May 22, 2000

(87) PCT Pub. No.: WO99/00073
PCT Pub. Date: Jan. 7, 1999

(30) Foreign Application Priority Data

Jun. 28, 1997 (GB) .............................. 9713624

(51) Int. Cl.$^7$ ................................. A61F 2/06
(52) U.S. Cl. ................ 623/1.25; 623/1.1; 623/1.24
(58) Field of Search ................ 623/1.1, 1.24, 623/1.25; 606/192–194, 198; 600/207

(56) References Cited

U.S. PATENT DOCUMENTS

| 3,631,854 A | | 1/1972 | Fryer | |
|---|---|---|---|---|
| 5,156,620 A | | 10/1992 | Pigott | |
| 5,370,691 A | * | 12/1994 | Samson | 606/194 |
| 5,507,770 A | * | 4/1996 | Turk | 606/198 |
| 5,524,633 A | * | 6/1996 | Heaven et al. | 600/207 |
| 5,529,653 A | | 6/1996 | Glastra | |
| 5,534,024 A | * | 7/1996 | Rogers et al. | 623/1.1 |
| 6,036,640 A | * | 3/2000 | Corace et al. | 600/207 |

FOREIGN PATENT DOCUMENTS

| EP | 0 441 516 A2 | 8/1991 |
|---|---|---|
| EP | 0 617 930 A1 | 10/1994 |
| WO | WO 97/19653 | 6/1997 |

* cited by examiner

Primary Examiner—Julian W. Woo
(74) Attorney, Agent, or Firm—Craig A. Fieschko, Esq.; DeWitt Ross & Stevens S.C.

(57) ABSTRACT

An expandable device, e.g. a stent for insertion into a passage, e.g. a blood vessel or artery, is disclosed. The device has a body (20) formed of a flexible material. The body is convertible from a collapsed condition in which it is of a size to be inserted into the passage into an expanded condition in which the body (20) is fixed relative to the passage. A passage (28) is provided within the body so as to extend over at least a region of the latter. An inlet (32) is provided in the body (20) in communication with the passage therein. The inlet (32) enables a rigidifying material to be introduced into the passage (28) in the body (20) so that at least the region of the body (20) in which the passage is provided can be rigidified whereby to maintain the body in its expanded condition.

30 Claims, 3 Drawing Sheets

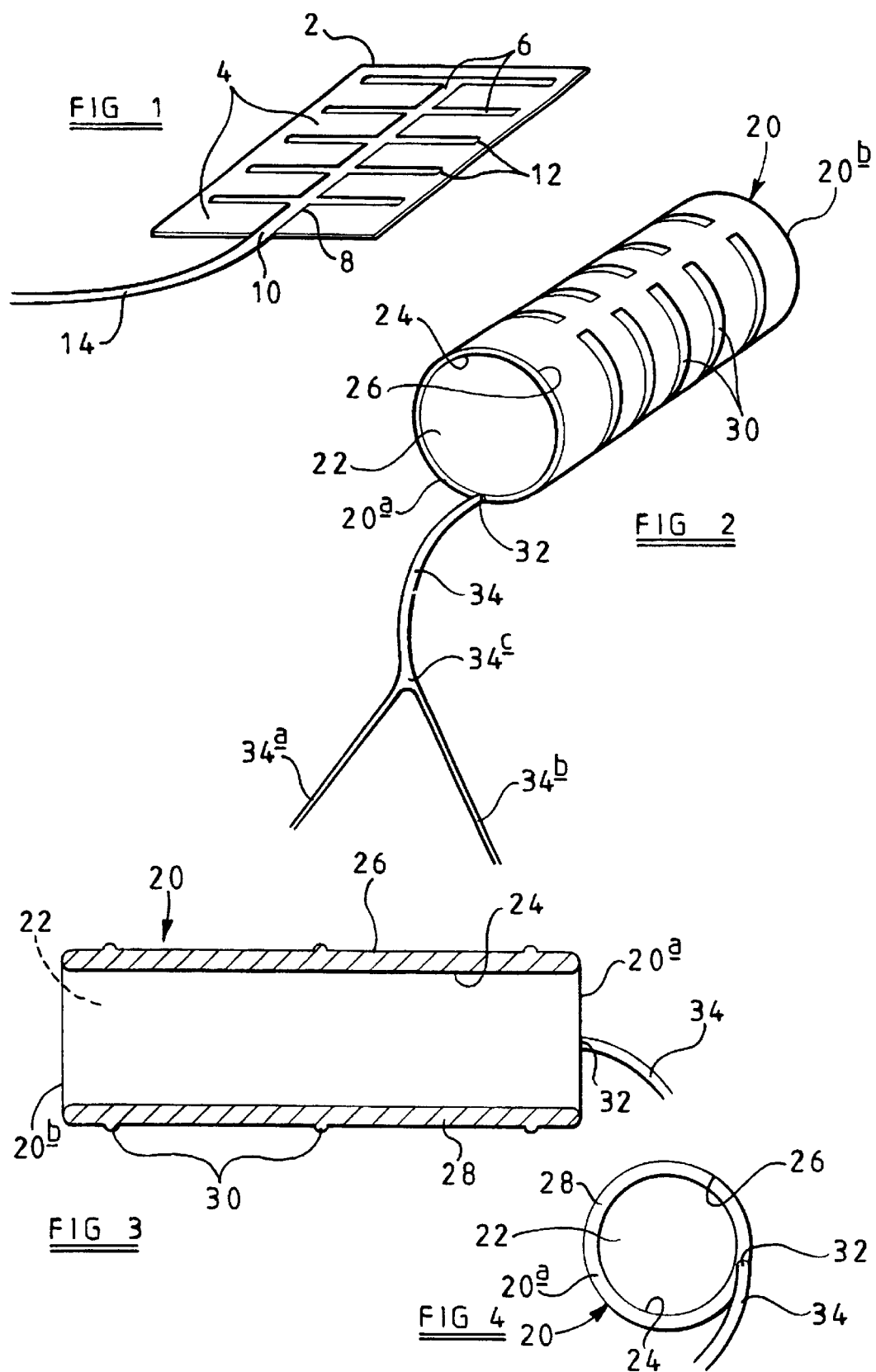

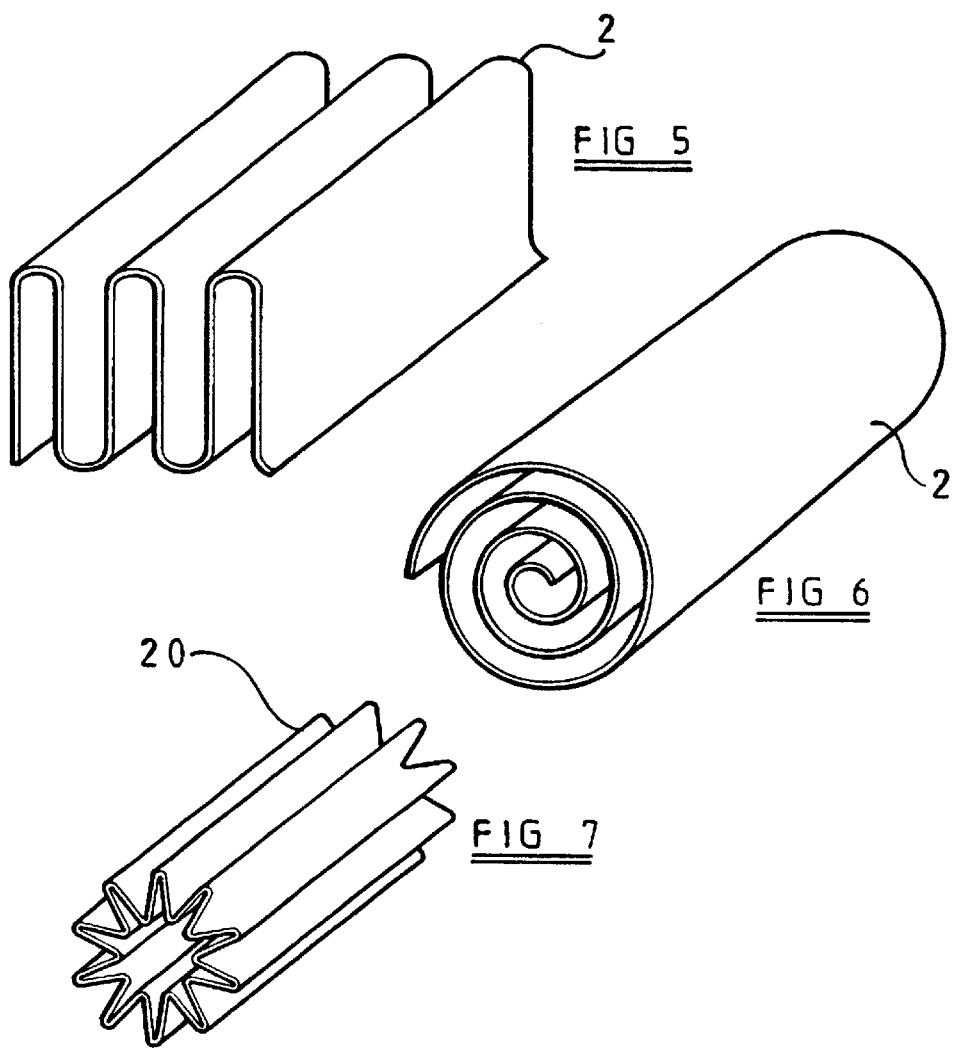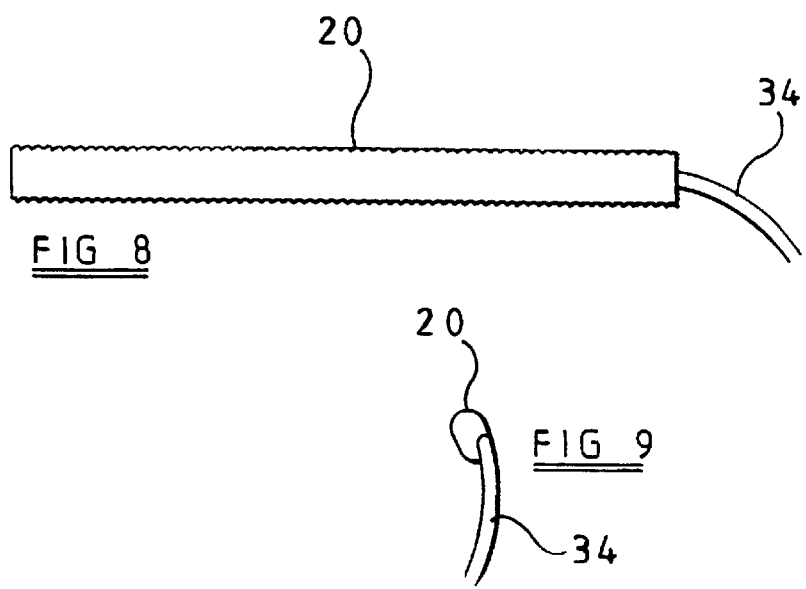

EXPANDABLE DEVICE

BACKGROUND OF THE INVENTION

1. Field of the Invention

This invention relates to an expandable device for insertion into a passage for the purpose of dilating the passage and/or maintaining it open, or occluding the passage and is more particularly concerned with an expandable device for use in medical applications where it can be used to dilate or maintain the luminal patency of arteries and other vessels which may have become partially or completely blocked, or to occlude undesired passages or openings such as between certain arteries or between heart chambers.

2. Description of the Prior Art

The use of expandable devices for insertion into a passage is particularly widespread in the medical field, where such devices are generally referred to as stents. Such stents are generally constructed of metal wire which may be braided (EP-A-0183372), wound (WO/9315661) or knitted (WO94/12136), or alternatively from tubing having perforated walls (WO95/03010).

Current stents are either balloon expanding or self expanding. Balloon expanding stents are the most common and rely on a balloon temporarily placed within the previously compacted stent to distend the stent radially and so lodge the stent firmly against the wall of the vessel within which it is located. However, problems can arise if there is any elastic recoil (i.e. radial contraction) of the stent once the balloon is removed.

Self expanding stents are made from a more elastic material which is constrained to a small diameter for insertion but which will expand to a larger diameter when deconstrained, without the need for any expanding means. Self-expanding stents made of shape-memory material are also known (see for example EP-A-066065). A medical practitioner must be careful in selecting an appropriate stent for each procedure, since situations may arise in which the outward pressure of the stent on the vessel is too great, causing physiological damage, or too small, resulting in dislodgement of the stent.

BRIEF SUMMARY OF THE INVENTION

It is an object of the present invention to provide an expandable device which can be fixed in its expanded condition in a passage, so as to minimise movement of the expanded device in the passage.

According to a first aspect of the present invention, there is provided an expandable device for insertion into a passage, said expandable device comprising a body formed of at least one flexible material, said body being convertible from a collapsed condition in which it is of a size to be inserted into the passage into an expanded condition in which the body is fixed relative to the passage, passage means in said body and extending over at least a region of the body, and inlet means communicating with said passage means to enable a rigidifying material to be introduced into said passage means so that, in use, at least said region of said body can be rigidified whereby to maintain the body in its expanded condition.

Preferably, the body is formed of at least one flexible sheet material. Said at least one flexible sheet material may be elastomeric or non-elastomeric. In cases where the body is formed of two or more flexible sheet materials, each may be elastomeric or non-elastomeric. Said at least one flexible sheet material may be tubular or include a tubular region.

Advantageously, the body in the collapsed condition occupies substantially the same volume as the at least one sheet material. Preferably, the inlet means is closable. Closure may be achieved by, for example, providing the inlet means with a heat-sealable closure, or alternatively the inlet means may be a self-sealing valve.

The device may also include filler means, such as an elongate tube, said filler means communicating with said passage means in the body via the inlet means. The filler means may be used to expand the body of the device and/or introduce the rigidifying material into the body through the inlet means. Preferably, the filler means is separable from the remainder of the device.

According to a second aspect of the present invention, there is provided an expandable device according to said first aspect of the present invention in combination with a rigidifying material for introduction into said passage means through said inlet means.

According to a third aspect of the present invention, there is provided a method of positioning an expandable device according to said first aspect in a passage, comprising the steps of:

(a) introducing into the passage an expandable device according to said first aspect of the present invention with the body being in a collapsed condition;

(b) converting the body into an expanded condition so that it is fixed relative to a sidewall of the passage; and (c) causing the flowability of rigidifying material introduced into the passage means to be decreased so as to maintain the body in its expanded condition.

Such positioning may be effected to (i) dilate or (ii) occlude the passage, or (iii) maintain the passage at an existing dilation. Additionally, such positioning may be effected to prevent ingress of material into the passage (eg. growths such as tumours in medical applications) and/or egress of material out of the passage, for example, if the passage is damaged (eg. aneurysm).

The body of the device may be inserted so as to be wholly within the passage, in which case fixing of the body relative to the passage is achieved by engagement of a sidewall of the body with the sidewall of the passage.

Alternatively, the body of the device may be inserted so as to be partially located within the passage, in which case said fixing may be achieved by expansion of at least one end of the body located externally of the passage, as an alternative to or in addition to the method of fixing described in the immediately preceding paragraph. Preferably, said fixing is achieved by expansion of opposite ends of the body externally of respective opposite ends of the passage, particularly where said passage is an opening such as between certain arteries or between heart chambers.

The rigidifying material may be a chemically reactive liquid or other fluid which can be caused to solidify, gel or otherwise set or experience an increase in its viscosity when in the passage means in the body. For example, the flowable rigidifying material may be selected from a flowable polymerisable monomer or monomer mixture or a flowable prepolymer, such as an epoxy resin, a silicone elastomer, a cyanoacrylate or methacrylate.

The rigidifying material itself may be used to effect step (b) above by introducing it under pressure into the passage means in the body. However, a hydraulic or pneumatic pressurising medium may be used for this purpose in addition to or instead of the rigidifying material. Additionally or alternatively, a balloon catheter may be used to move the body into its expanded condition.

In one embodiment, the sidewall of the body which engages with the sidewall of the passage in use, is formed of at least one flexible sheet material. The passage means may be disposed inwardly or outwardly of said at least one flexible sheet material or between the flexible sheet materials when more than one is provided. The passage means may be defined at least partly by said at least one sheet material. The passage means may be defined by one or a series of channels extending over at least one surface of said at least one sheet material. When a series of channels is provided, said channels need not be in communication, in which case more than one inlet and filler means may be provided.

Examples of suitable flexible materials for the body include polyesters and polyurethanes. The flexible material may be chemically coated. In particular, the sidewall which engages against the sidewall of the passage may be coated. For example, in medical applications, the sidewall may be coated with cytotoxic agents to treat tumours and/or to discourage tumour growth into the passage. Alternatively, or in addition, a coating of a relatively inert nature may be used to prevent or limit adverse biological reactions between the passage and the body. Examples of such coatings may comprise diamond-like carbon, a ceramic or metals (eg. gold, silver, platinum).

The channel or channels may be defined by two superimposed sheet materials which are sealed together at selected regions so that unsealed regions of the sheet materials define wall of the channel or channels. Alternatively, the channel or channels may be defined on a surface of the sheet material by sealing longitudinal side edges of a suitably shaped strip or strips of flexible material to said surface.

Two or more bodies may be connected in series. Each of the bodies may be provided with its own inlet and filler means so that, in use, each body may be expanded and/or rigidified to a different degree.

Embodiments of the present invention will now be described, by way of example, with reference to the accompanying drawings, in which:

BRIEF DESCRIPTION OF THE DRAWINGS

FIG. 1 is a view of a first embodiment of a device according to the first aspect of the present invention, FIGS. 2 to 4 show a second embodiment of a device according to the first aspect of the present invention in an expanded condition, FIGS. 5 to 7 show schematically how bodies of devices according to the present invention may be collapsed, FIGS. 8 and 9 show the device of FIGS. 2 to 4 in a collapsed condition.

FIGS. 13 and 14 show schematically the use of the device of FIG. 12 as a

DETAILED DESCRIPTION OF THE INVENTION

Figure 10:
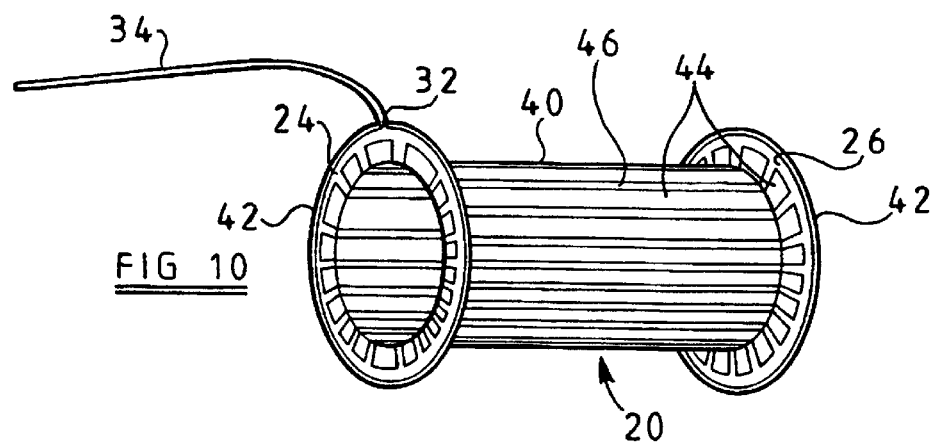
FIG. 10 is a view of a third embodiment of a device according to the first aspect of the present invention in an expanded condition.

Referring to FIG. 1, a body 2 of an expandable device comprises two superimposed flexible sheet materials which are sealed together at selected regions 4 so that unsealed regions 6 of the sheet materials define walls of channels therebetween. The sheet materials are polymeric (eg. a polyester or polyurethane) and are sealed by, for example, radio-frequency welding, ultrasonic welding or electrical resistance heating or by moulding or casting processes.

A main channel 8 extends from an inlet 10 at a proximal edge of the superimposed sheet materials towards a distal edge thereof, with subsidiary channels 12 extending at intervals transversely of the main channel 8 and in communication therewith. A filler tube 14 is attached to the body 2 at the inlet 10 and is in communication with the channels 8, 12. The body 2 is shown in an expanded condition.

In use, the device is inserted into a passage (eg. blood vessel) with the body 2 in a collapsed condition (described more fully hereinafter) and a liquid gelling agent is passed through the filler tube 14 into the channels 8, 12 of the body 2 so expanding the body 2. In the passage, the body 2 will not be flat as shown in FIG. 1, but will bend so as to adopt the shape of a sidewall of the passage. When the gelling agent sets, the body 2 will be maintained in that shape. The body 2 is then sealed at the inlet 10 and the filler tube 14 separated from the body 2 and removed from the passage.

In an alternative embodiment (not shown), the subsidiary channels 12 are slanted so as to form a series of parallel V-shapes intersecting at the main channel 8 (i.e. herringbone pattern). In other embodiments (not shown), the subsidiary channels are arranged to produce a specific expansion geometry in, for example, particular parts of the anatomy. Specifically, in a bifurcated tubular graft (eg. for the interconnection of vascular components such as the femoral arteries to the iliac arteries or in the case of abdominal aortic aneurysms where the aorta must be internally bypassed using the graft to make connections to the iliac arteries and exclude an aneurysmal sac existing at the lower end of the aorta), insertion is achieved with one branch retracted in another. The channels are arranged to ensure that on expansion, the retracted branch is retrieved from the other branch.

Referring to FIGS. 2, 3 and 4, the body 20 of the device is tubular and in the expanded condition shown has a passage 22 therethrough. An inner sheet material 24 is sealed to an outer sheet material 26 at the proximal and distal ends 20a, 20b, respectively, of the tubular body 20, so as to form a single channel 28 therebetween extending over the whole of the area of the body. The outer sheet material 26 has a number of regions which form part-circumferential ridges 30 when the body 20 is in an expanded condition. An inlet 32 to the channel 28 is provided at the proximal end 20a of the body 20, said inlet 32 being connected to a filler tube 34, which divides into two tubes 34a, 34b at a branch point 34c.

In use, the device in its collapsed condition is inserted into a passage (not shown) and positioned as desired. A different component of a twocomponent reactive liquid is then fed into each of the two tubes 34a, 34b so that the two components combine to form a gelling mixture in the filler tube 34 which is then forced into the channel 28. The body 20 of the device becomes expanded, with the ridges 30 being formed at the same time, and subsequently rigidified. The passage is maintained open by virtue of the passage 22 through the body 20. The ridges 30 on the outer sheet material 26 help maintain the body 20 in position in the passage. Alternatively, the body may be expanded by pneumatic means such as balloon catheter (not shown). In this case, the deflated balloon catheter is placed in the passage 22 through the body 20 before the device is placed in the passage. The body 20 is then expanded by inflation of the balloon catheter before the rigidifying material is introduced into the channel 28. When the body 20 is sufficiently rigid, the balloon catheter is deflated and can be withdrawn.

Referring to FIGS. 5 to 7, the body 2, 20 of the device is capable of occupying a very small volume in its collapsed state relative to its volume in its expanded state. A non-tubular body 2 (eg. that exemplified in FIG. 1) may be corrugated so as to form compacted pleats (FIG. 5) or rolled so as to form a spiral (FIG. 6). Tubular bodies 20 (eg. that exemplified in FIG. 2) can be longitudinally creased and radially compacted (FIG. 7). The body 2, 20 may also be formed into a helix (not shown) by constraining the proximal end and rotating the distal end.

The embodiments described above are particularly suitable for medical applications such as aneurysm repair, improving the luminal patency of an occluded vessel and preventing intimal hyperplasia (or occlusive tumorous growth in non-vascular vessels). A comparison of FIGS. 7 and 8 with FIGS. 2 and 3 illustrates the large difference in volume between the expanded and collapsed states. The small volume of the collapsed body 20 (FIGS. 7 and 8) allows it to be introduced into, for example, the vascular system in a catheter, with minimal invasive surgery.

Figure 11:
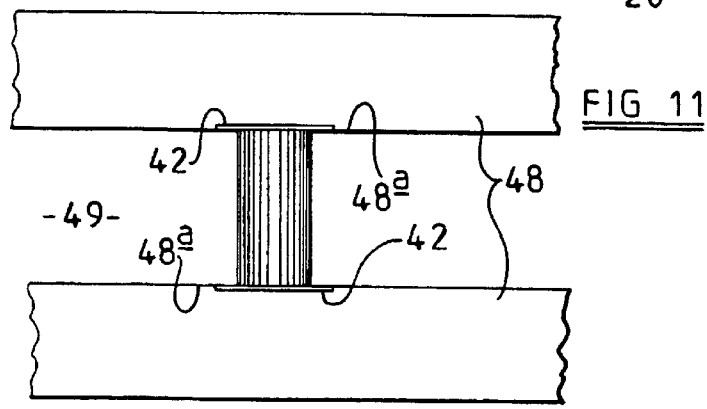
FIG. 11 shows the device of FIG. 10 in use.

Referring to FIG. 10, similar parts to those in the second embodiment (FIGS. 2 to 4) are accorded the same reference numerals. The body 20 of the device has a tubular region 40 integrally formed with an outwardly extending annular flange 42 at the proximal 20a and distal 20b ends of the tubular region 40. The inner flexible sheet material 24 is sealed to the outer flexible sheet material 26 in strips 44 at intervals around the body 20, said sealed strips 44 extending longitudinally over the length of the tubular region 40 of body 20 and radially over an inner part of the flanges 42. As a result, a series of longitudinal channels 46 between the inner 24 and outer 26 sheet materials are interconnected on the flanges 42. The channels 46 are in communication with the inlet 32 and filler tube 34. FIG. 11 shows the device of FIG. 10 in use to interconnect two vessels 48 through tissue 49 so as to allow flow between the vessels. Depending on the degree of defect, there may be an occluded passage between the vessels 48 or no passage at all. It may be necessary to make an opening in one or both vessels to enable correct positioning of the device. In the expanded condition shown, each of the annular flanges 42 engages with a sidewall 48a of a different one of the vessels 48 so as to fix the device in position relative to the vessels 48.

Figure 12:
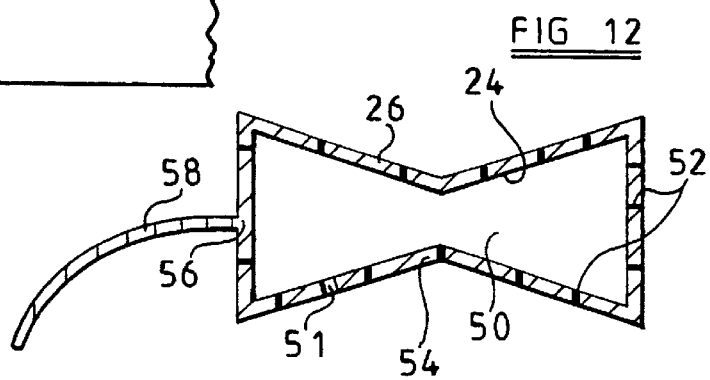
FIG. 12 is a view of a fourth embodiment of a device according to the first aspect of the present invention in an expanded condition.

Referring to FIG. 12, the inner flexible sheet material 24 is sealed so as to form an enclosed volume 50. A vent 51 allows the body of the device to be collapsed. The outer flexible sheet material 26 is connected to the inner sheet material 24 by a series of ribs 52, so that a single channel 54 is formed between the sheet materials 24, 26, said channel 54 being in communication with the inlet 56 and filler tube 58. Both flexible sheet materials are non-elastomeric. On filling with rigidifying material, the body 59 adopts a diabolo shape (as shown in FIG. 12).

Figure 13:
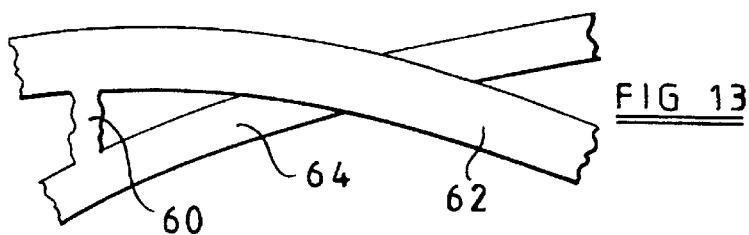
Figure 14:
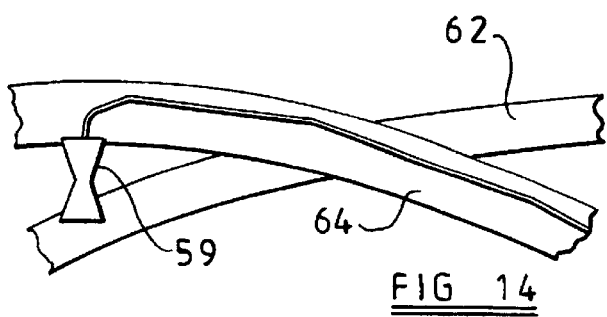

In FIG. 13, a patent ductus arteriosus 60 is shown between an aorta 62 and a pulmonary artery 64, in a condition known as patent ductus. In order to occlude the patent ductus arteriosus 60, the device of FIG. 12 is passed through the patent ductus arteriosus 60 from the arterial side or the venous side of the vascular system, both techniques being commonly used. In order to facilitate passage through the ductus, the body 59 is collapsed during insertion. When the body 59 is expanded, it is engaged with a sidewall of both the aorta 62 and pulmonary artery 64 (see FIG. 14). Introduction of the rigidifying material maintains the body 59 in position.

What is claimed is:

1. An expandable device for insertion into a passage, said expandable device comprising:
    a. a body formed of at least one flexible material, said body being convertible from a collapsed condition in which it is of a size to be inserted into the passage into an expanded condition in which the body is fixed relative to the passage,
    b. passage means in said body, said passage means including a main channel in communication with a purality of channels extending transversely from the main channel, extending over at least a region of the body, and being spaced by portions of the body,
    c. inlet means communicating with said passage means, and
    d. flowable rigidifying material introducable into the passage means, the material rigidifyin within the passage means to thereby maintain the body in the expanded condition.

2. A device as claimed in claim 1, wherein the body is formed of at least one flexible sheet material.

3. A device as claimed in claim 1, wherein the inlet means is closable.

4. A device as claimed in claim 1, wherein the sidewall of the body which engages with the sidewall of the passage in use, is formed of at least one flexible sheet material.

5. A device as claimed in claim 1, wherein the passage means is disposed inwardly or outwardly of said at least one flexible sheet material or between the flexible sheet materials when more than one is provided.

6. The expandable device of claim 1 wherein the flowable rigidifying material comprises at least one component selected from the following group:
    a. a polymerizable monomer; and
    b. a pre-polymer.

7. The expandable device of claim 1 wherein the flowable rigidifying material includes at least one of:
    a. epoxy resin;
    b. a silicon elastomer;
    c. a cyanoacrylate; and
    d. a methacrylate.

8. The expandable device of claim 1 wherein the flowable rigidifying material comprises at least two components wherein the components rigidify after their combination occurs.

9. The expandable device of claim 1 wherein the body is tubular, with an interior passage extending between opposing ends of the body when the body is in the expanded condition.

10. A device for insertion in a body passage comprising a thin fabric formed with a plurality of flexible channels discretely spaced from each other and having a first condition in which said thin fabric is collapsed and a second condition in which said thin fabric is expanded to conform to a shape of at least a part of said passage when said thin fabric is disposed within said passage, said channels including a main channel in communication with subsidiary channels transversely extending from said main channel and said channel having a flowable rigidifying material therein, wherein rigidification of the material fixes the channels surrounding the material against flexion.

11. The device of claim 10 wherein said thin fabric includes two superimposed sheets, said sheets having sealed regions and unsealed regions, said sheets being joined along said sealed regions and forming said channels in said unsealed regions.

12. The device of claim 10 wherein said channels form ridges along said unsealed regions when filled with said rigidifying matter, said ridges being adapted to engage said passage to maintain said device within said passage.

13. The device claim 10 wherein said channels include an inlet adapted to receive said rigidifying matter, and main channel in communication with said inlet.

14. The device of claim 10 wherein said thin fabric is arranged and constructed in said second condition to maintain said passage open.

15. An expandable device for insertion into a lumen, the device:
   a. being formed of flexible material;
   b. being convertible:
      (1) from a collapsed condition wherein the device is insertable into the lumen,
      (2) into an expanded condition wherein the device extends over and supports the surface of the lumen, and wherein the device at least partially encircles an interior passage extending along the lumen; and
   c. having areas thereon spaced by expandable channels, said channels including a main channel in communication with subsidiary channels extending transversely from said main channel, wherein the expandable channels have fluid rigidifying material therein which maintains the device in the expanded condition, the material rigidifying to fix the device in the expanded condition.

16. The expandable device of claim 15 wherein the expandable channels have widths shorter than the spacing between the expandable channels.

17. The expandable device of claim 15 wherein the expandable channels, when expanded, define a framework of at least substantially tubular shape.

18. The expandable device of claim 15 wherein the expandable channels extend about the interior passage in an at least substantially circumferential direction.

19. The expandable device of claim 15 wherein the device is tubular with the interior passage extending therein between opposing ends of the device, the interior passage being collapsed when the device is in its collapsed condition.

20. The expandable device of claim 15 wherein the device is sheetlike with opposing sides when in its collapsed condition, with the device curving to adjacently situate its opposing sides to define the interior passage when in its expanded condition.

21. An expandable device for insertion into a lumen, the device:
   a. including one or more flexible channels expandable:
      (1) from a collapsed state, to
      (2) an expanded state wherein the channels define a framework which at least partially surrounds an interior passage extending along the lumen; and
   b. webs of flexible material spacing the channels, wherein the device may be drawn through the lumen when the channels are in the collapsed state, and the channels may subsequently be put in their expanded state to have the framework and webs extend about and support the surface of the lumen,
   and wherein the channels are filled with fluid rigidify material, the material flowing to inflate the channels to their expanded state and subsequently rigidifying into a nonflowing state to fix the channels against collapse.

22. The expandable device of claim 21 wherein the channels have widths shorter than the spacing between the channels.

23. The expandable device of claim 21 wherein the framework has at least substantially tubular shape.

24. The expandable device of claim 21 wherein the channels extend in an at least substantially circumferential direction about the interior passage of the framework.

25. The expandable device of claim 21 wherein the device is sheetlike with opposing sides when in its collapsed state, with the device curving about the interior passage with its opposing sides adjacently situated when in its expanded condition.

26. An expandable device for insertion into a lumen, the device:
   a. including expandable channels having widths spaced by one or more areas of flexible material, and wherein the spacing between the expandable channels is at least as great as their widths, and
   b. being convertible between:
      (1) a collapsed state wherein the expandable channels are at least substantially empty and the device is movable within the lumen, and
      (2) an expanded state wherein the expandable channels are filled with flowable rigidifying material to extend along and support the surface of the lumen, with the expandable channels at least partially encircling and maintaining a passage within the lumen, and wherein the rigidifying material rigidifies to a non-flowine state to fix the channels in place.

27. The expandable device of claim 26 wherein the expandable channels, when expanded, define a framework of at least substantially tubular shape.

28. The expandable device of claim 26 wherein the expandable channels extend in an at least substantially circumferential direction about the passage.

29. The expandable device of claim 26 wherein the device is tubular with the passage extending therein between opposing ends of the device, the passage being collapsed when the device is in its collapsed state.

30. The expandable device of claim 26 wherein the device is sheetlile with opposing sides when in its collapsed state, with the device curving about the interior passage with adjacently situated sides when in its expanded state.

* * * * *